US008183305B2

(12) United States Patent
Neffgen et al.

(10) Patent No.: US 8,183,305 B2
(45) Date of Patent: May 22, 2012

(54) RADIOPAQUE INFILTRANT

(75) Inventors: Stephan Neffgen, Hamburg (DE); Swen Neander, Hamburg (DE); Dierk Lübbers, Halstenbek (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 123 days.

(21) Appl. No.: 12/537,015

(22) Filed: Aug. 6, 2009

(65) Prior Publication Data

US 2010/0041789 A1 Feb. 18, 2010

(30) Foreign Application Priority Data

Aug. 13, 2008 (EP) ..................................... 08014437

(51) Int. Cl.
*A61F 2/00* (2006.01)
(52) U.S. Cl. ........................................ 523/115; 523/117
(58) Field of Classification Search .................. 523/117, 523/115
See application file for complete search history.

(56) References Cited

U.S. PATENT DOCUMENTS

| 3,518,762 | A | * | 7/1970 | Takeuchi ................... 433/228.1 |
| 3,709,866 | A | * | 1/1973 | Waller ............................ 522/96 |
| 3,903,055 | A | * | 9/1975 | Buck .............................. 526/194 |
| 4,065,624 | A | * | 12/1977 | Prucnal et al. ................. 428/522 |
| 4,097,994 | A | * | 7/1978 | Reaville et al. ............... 523/115 |
| 4,119,610 | A | * | 10/1978 | Kaelble ....................... 526/292.2 |
| 4,136,138 | A | * | 1/1979 | Dombroski et al. ........... 525/265 |
| 4,150,485 | A | * | 4/1979 | Lee et al. ...................... 523/115 |
| 4,308,014 | A | * | 12/1981 | Kawahara et al. ............. 523/115 |
| 4,327,014 | A | * | 4/1982 | Kawahara et al. ............. 523/116 |
| 4,341,691 | A | * | 7/1982 | Anuta ............................ 523/116 |
| 4,358,549 | A | * | 11/1982 | Randklev ...................... 523/117 |
| 4,440,878 | A | * | 4/1984 | Kawahara et al. ............. 523/116 |
| 4,454,258 | A | * | 6/1984 | Kawahara et al. ............. 523/116 |
| 4,511,732 | A | * | 4/1985 | Hicks ............................ 560/221 |
| RE32,073 | E | * | 1/1986 | Randklev ...................... 523/117 |
| 4,622,367 | A | * | 11/1986 | Horak et al. ................... 525/381 |
| 4,631,300 | A | * | 12/1986 | Hicks ............................ 522/100 |
| 4,774,267 | A | * | 9/1988 | Weintraub ..................... 523/116 |
| 5,276,070 | A | * | 1/1994 | Arroyo .......................... 523/117 |
| 5,505,956 | A | * | 4/1996 | Kim et al. ...................... 424/448 |
| 5,883,153 | A | * | 3/1999 | Roberts et al. ................ 523/116 |
| 6,028,125 | A | * | 2/2000 | Combe et al. ................. 523/116 |
| 6,197,846 | B1 | * | 3/2001 | Combe et al. ................. 523/116 |
| 6,339,113 | B1 | * | 1/2002 | Han et al. ...................... 522/100 |
| 6,387,981 | B1 | * | 5/2002 | Zhang et al. .................. 523/117 |
| 6,573,312 | B2 | * | 6/2003 | Han et al. ...................... 523/116 |
| 6,583,197 | B1 | * | 6/2003 | Wada et al. ..................... 522/84 |
| 6,620,859 | B2 | * | 9/2003 | Warford et al. ................ 523/115 |
| 6,623,823 | B1 | * | 9/2003 | Onwumere ................. 428/36.91 |
| 6,695,617 | B1 | * | 2/2004 | Wellinghoff et al. ....... 433/202.1 |
| 6,797,767 | B2 | * | 9/2004 | Stannard et al. .............. 524/559 |
| 6,852,775 | B1 | * | 2/2005 | Soglowek et al. ............ 523/109 |
| 7,235,602 | B2 |   | 6/2007 | Klettke et al. |
| 7,314,610 | B2 | * | 1/2008 | Loveridge ...................... 424/9.7 |
| 7,371,782 | B2 | * | 5/2008 | Stannard et al. .............. 522/171 |
| 7,553,881 | B2 |   | 6/2009 | Salz et al. |
| 7,851,515 | B2 | * | 12/2010 | Salz et al. ...................... 523/115 |
| 7,915,324 | B2 | * | 3/2011 | Eckert et al. .................. 523/116 |
| 7,977,404 | B2 | * | 7/2011 | Wolter et al. .................. 523/116 |
| 2002/0072551 | A1 | * | 6/2002 | Han et al. ...................... 523/118 |
| 2002/0156152 | A1 | * | 10/2002 | Zhang et al. .................. 523/115 |
| 2006/0069181 | A1 | * | 3/2006 | Thalacker et al. ............ 523/116 |
| 2006/0235556 | A1 | * | 10/2006 | Resnick et al. ................. 700/98 |
| 2006/0241203 | A1 |   | 10/2006 | Ruppert et al. |
| 2006/0264532 | A1 | * | 11/2006 | Meyer-Luckel et al. ...... 523/115 |
| 2007/0111152 | A1 | * | 5/2007 | Primus et al. ..................... 433/9 |
| 2007/0142495 | A1 | * | 6/2007 | Neffgen et al. ................ 523/116 |
| 2007/0160958 | A1 | * | 7/2007 | Belikov et al. ................ 433/215 |
| 2008/0057000 | A1 | * | 3/2008 | Loveridge ...................... 424/9.7 |
| 2008/0280260 | A1 | * | 11/2008 | Belikov et al. ................ 433/215 |
| 2009/0297612 | A1 | * | 12/2009 | Koole et al. ................... 424/489 |

FOREIGN PATENT DOCUMENTS

| DE | 19638068 | | 3/1998 |
| DE | 202008006814.2 | | 11/2009 |
| EP | 1570831 | | 3/2004 |
| EP | 1720506 | | 3/2005 |
| EP | 1849450 | | 4/2006 |
| EP | 1872767 | | 6/2006 |
| EP | 1714633 | | 7/2006 |
| EP | 1854445 | A1 * | 11/2007 |
| EP | 1285947 | | 2/2008 |
| EP | 2145613 | A1 * | 1/2010 |
| EP | 2226061 | A1 * | 9/2010 |
| WO | WO02/062901 | | 8/2002 |
| WO | WO02/066535 | | 8/2002 |
| WO | WO2004/017928 | | 3/2004 |
| WO | WO2005/086911 | | 9/2005 |
| WO | WO2005/121200 | | 12/2005 |
| WO | WO2006/031972 | | 3/2006 |
| WO | WO2007/131725 | | 11/2007 |
| WO | WO 2007131725 | A1 * | 11/2007 |

OTHER PUBLICATIONS

English Abstract of DE19638068, Published Mar. 19, 1998.
English Abstract of WO05/121200 published Dec. 22, 2005.
English Abstract of EP1570831, published Mar. 2, 2004.
US2007142495 is the English equivalent of EP1570831, published Mar. 2, 2004. English Abstract of EP1714633 published Jul. 4, 2006.
US2006241203 is the English equivalent of EP 1714633 published Jul. 4, 2006.
English Abstract of EP1720506 published Mar. 2, 2005.
US2007142495 is the English equivalent of EP1720506.
English Abstract of EP1849450 published Apr. 28, 2006.
US7553881 is the English equivalent of EP1849450 published Apr. 28, 2006.

(Continued)

*Primary Examiner* — James J Seidleck
*Assistant Examiner* — Peter A Salamon
(74) *Attorney, Agent, or Firm* — Casimir Jones, S.C.

(57) ABSTRACT

The invention provides an infiltrant for dental application that comprises crosslinking monomers, having a penetration coefficient PC>50 cm/s. In accordance with the invention the infiltrant comprises at least one nanoscale radiopaque filler and/or radiopaque organic compound, while ensuring sufficient contrast to surrounding tooth and bone tissue in X-ray diagnostics.

50 Claims, No Drawings

OTHER PUBLICATIONS

English Abstract of WO 02/066535 published Aug. 29, 2002.
US 7235602 is the English Equivalent of WO02/066535 published Aug. 29, 2002.
Buckton G., Interfacial phenomena in drug delivery and targeting. Chur, 1995.
cf. Römpp Chemie Lexikon, Georg Thieme Verlag, 1990, p. 1711.
Fan, et al. "Penetrativity of sealants" J. Dent. Res., 1975, 54: 262-264.
ISO 3219:1993, section 3 on p. 1 under "Notes".
K.J. Ivin, T. Saegusa, (eds.), vol. 2, Elsevier Appl. Sci. Publ., London 1984.

* cited by examiner

RADIOPAQUE INFILTRANT

This application claims the benefit of European Application No. 08 014 437.1, filed Aug. 13, 2008.

The invention relates to an infiltrant for dental application that comprises crosslinking monomers and also to its use in preventing and/or treating (sealing) carious enamel lesions.

Carious enamel lesions here are essentially instances of carious damage that extend in the dental enamel but have not yet led to cavitation (hole formation). Carious enamel lesions are demineralized regions of the dental enamel that may have a depth of up to about 2-3 mm.

The published international application WO 2007/131725 A1 has disclosed treating carious enamel lesions by an infiltration method and infiltrants, to prevent cavitation and obviate the restoration with dental composites that is otherwise typically practiced. In the infiltration method, after any superficial remineralized layer present has been removed, the lesion is contacted with an infiltrant that is composed substantially of monomers, which then infiltrate. When the infiltrant has infiltrated the lesion, the monomers are polymerized by means of photoactivation. This seals the lesion. The progression of the caries is halted.

Infiltration requires specific monomers or monomer mixtures, since known dental adhesives for dental composites (also known as bondings) penetrate too slowly and/or inadequately into the lesion and/or penetrate (or infiltrate) the lesion completely. WO 2007/131725 A1 describes the use of monomers or monomer mixtures whereby the infiltrant has a penetration coefficient PC>50.

To be distinguished from these are the dental materials known from the prior art, examples being the dental restoration compomers known from DE-A-196 38 068 or the modelable compositions known from EP-A-1 570 831 and EP-A-1 872 767, which, as elucidated briefly below, have a PC well below 50 cm/s. They were developed and optimized in order to exhibit maximum adhesion to the tooth substance, but not deep infiltration. It is therefore not surprising that these materials, not least on the basis of their low penetration capacity, which is reflected in the PC, are unsuitable as infiltrants, since their penetration is merely superficial.

In principle it should be noted that the viscosities of the infiltrants of the invention that form part of the calculation of the PC (see below, equation 2), at less than 50 mPas, lie between that of liquids such as water (~1 mPas, 20° C.) or milk (~1.2 mPas, 20° C.) and edible oils (>~50 mPas, 25° C.).

For the compomer mixture I of the prior application DE-A-196 38 068 of the applicant, and with a view to the calculation of the PC [see below, equation 2, with the determinant factors of surface tension ($\gamma$), contact angle ($\theta$), and viscosity ($\eta$)], the result in the case of a dynamic viscosity of about 180 000 mPas, an assumed high wettability with a corresponding contact angle of virtually zero (cosine therefore 1), and a surface tension comparable with that from methacrylate monomers, of 30-40 mN/m, i,e., $$PC = \left[\frac{\gamma \cdot \cos\theta}{2\eta}\right] = \left[\frac{40 \text{ mN/m} \cdot 1}{2 \cdot 180\,000 \text{ mPas}}\right] = 0.01 \text{ cm/s},$$

is a PC value well below the >50 cm/s value claimed in accordance with the invention. In other words, the compomer mixtures of DE-A-196 38 068 are already unsuitable as infiltrants on the basis of the low penetration capacity.

The same applies to the low-viscosity dental materials of EP-A-1 570 831 and EP-A-1 872 767, whose examples show that they are definitely not fluid mixtures with potential suitability as infiltrants, but instead are solid, modelable pastes.

It is an object of the invention to create an infiltrant of the type specified at the outset that allows simple monitoring of the success of an infiltration that has been carried out.

The invention achieves the object with an infiltrant according to claim 1. Advantageous embodiments of the invention are disclosed in the dependent claims.

In one particularly preferred embodiment of the invention the infiltrants contain:
- at least 50% by weight of monomers,
- 1-30% by weight of radiopaque nanoscale filler and/or radiopaque organic compounds,
- optionally up to 20% by weight of solvent(s), and
- initiator, where
- 50-100% by weight of the monomers are crosslinking monomers, i.e., monomers having at least two polymerizable groups,
- the radiopaque filler is substantially unagglomerated and has a particle size of less than 500 nm, and
- the infiltrant has a penetration coefficient at room temperature of PC>50 cm/s and an ISO 4049 radio-opacity of at least 50% of aluminum.

Arriving at the present invention necessitates, for the skilled worker, steps a) and b), described below.

a) Recognizing the Disadvantage of the Prior-Art Infiltrants (Insufficient Radiopacity)

A disadvantage of the infiltrants known from the prior art (e.g., WO 2007/131725 A1) is their inadequate radiopacity. They are substantially translucent to X-rays and are therefore very difficult or impossible to discern in the event of an X-ray diagnosis. Accordingly one of the most important instruments for ascertaining the extent and the position of infiltrations that are present is deprived of its value. Apart from this, it is difficult, when using X-ray diagnostics, owing to the inadequate radiopacity of the infiltrants, to determine caries that may be progressing further beneath the infiltrated lesion, since such caries is very difficult or impossible to distinguish from the infiltrated region. In order to determine progressive caries, costly and inconvenient, precisely reproducible bitewing radiographs are then required, as are described in the German utility model application DE 202008006814.2.

The invention has recognized in a first step that dental regions restored by infiltration are not easy to identify by X-ray diagnostics and that through greater radiopacity of the infiltrant it might be possible to produce a degree of contrast to the surrounding healthy tooth and bone tissue and/or else to carious tooth and bone tissue that is sufficient for X-ray-diagnostic examination.

b) Provision of a Suitable Infiltrant Contrast Agent, Overcoming a Prejudice of the Art The inadequate contrasting as found for infiltrations does not arise in the case of the conventionally used dental materials of the kind employed in restoration or tooth replacement. The metallic restorations used in the prior art inherently generate a good contrast. The same applies to ceramic materials and polymeric composites, in which the pigments and/or fillers added primarily for reasons of increasing the mechanical strength and reducing the contraction provide a sufficient radiopaque contrast.

Suitable glass and nanoscale fillers and filler combinations for dental composites are known to the skilled worker and described in EP 1720506 A1, for example.

Nanoscale fillers had not been considered as a component for an infiltrant by a person skilled in the art in the field of the present invention, particularly not the skilled person in accordance with WO 2007/131725. Firstly, because that person did not recognize the problem set out under a), i.e., the problem (and hence the inventive solution to the unrecognized problem) did not present itself to him or her. Secondly, because, even if he or she had recognized the problem of the lack of radiopacity in infiltrants, he or she would not have found a solution in the field of conventional restoration materials without taking an inventive step. The reason for this is that the skilled person, on the basis of his or her art knowledge, necessarily assumed that nanoscale fillers would increase the viscosity of the infiltrant to an unfavorably severe extent. This assumption is based in particular on the property observed for liquid dental composites where the viscosity rises sharply when nanoscale fillers are added.

An increase in viscosity, however, would specifically not be desired or accepted by the skilled person, when using nanoscale fillers and infiltrants, since he or she, at the anticipated higher viscosity, is no longer able to assume sufficient penetration of the infiltrant into the enamel lesion. In other words, therefore, in the case of the known nanoscale fillers, the skilled person expects them to lower the penetration coefficient of an infiltrant to such a severe extent that its penetrativity is lost or severely impaired.

The present invention has found, surprisingly, that, contrary to this assumption, infiltrants with nanoscale fillers and/or organic compounds can be provided for as-intended use as an infiltrant for dental applications.

As demonstrated by the experimental examples of the present invention, the present invention does actually solve the technical problem addressed by the present invention. The experiments demonstrate that in the case of the infiltrants of the invention it is possible to combine sufficiently high penetration coefficients with a high radiopacity.

First of all a number of terms used in the context of the invention will be elucidated.

The term "infiltrant" refers to a liquid which as an uncured resin is able to penetrate into an enamel lesion (a porous solid). Following penetration, the infiltrant can be cured therein.

The penetration of a liquid (uncured resin) into a porous solid (enamel lesion) is described physically by the Washburn equation (equation 1, see below). With this equation it is assumed that the porous solid represents a bundle of open capillaries (Buckton G., Interfacial phenomena in drug delivery and targeting. Chur, 1995); in this case, the penetration of the liquid is driven by capillary forces.

$$d^2 = \left(\frac{\gamma \cdot \cos\theta}{2\eta}\right) r \cdot t \qquad \text{equation 1}$$

d distance by which the liquid resin moves
$\gamma$ surface tension of the liquid resin (with respect to air)
$\theta$ contact angle of the liquid resin (with respect to enamel)
$\eta$ dynamic viscosity of the liquid resin
r capillary radius (pore radius)
t penetration time The expression in parentheses in the Washburn equation is referred to as the penetration coefficient (PC, equation 2, see below) (Fan P. L. et al., Penetrativity of sealants. J. Dent. Res., 1975, 54: 262-264). The PC is composed of the surface tension of the liquid with respect to air ($\gamma$), the cosine of the contact angle of the liquid with respect to enamel ($\theta$), and the dynamic viscosity of the liquid ($\eta$). The greater the value of the coefficient, the faster the penetration of the liquid into a given capillary or into a given porous bed. This means that a high value of PC can be obtained through high surface tensions, low viscosities, and low contact angles, the influence of the contact angle being comparatively small.

$$PC = \frac{(\gamma \cdot \cos\theta)}{2\eta} \qquad \text{equation 2}$$

PC penetration coefficient
$\gamma$ surface tension of the liquid resin (with respect to air)
$\theta$ contact angle of the liquid resin (with respect to enamel)
$\eta$ dynamic viscosity of the liquid resin Surprisingly it has been found that infiltrants comprising nanoscale fillers can have penetration coefficients above 50, preferably above 100 cm/s.

The nanoscale fillers (i) that are used and are suitable in accordance with the invention are metal, semimetal or mixed-metal oxides, silicates, nitrides, sulfates, titanates, zirconates, stannates, tungstates, phosphates, halides or a mixture of these compounds. The group of the semimetals, whose properties (especially appearance and electrical conductivity) are situated between those of the metals and of the nonmetals, include boron, silicon, germanium, arsenic, antimony, bismuth, selenium, tellurium, and polonium (cf. Römpp Chemie Lexikon, Georg Thieme Verlag, 1990, p. 1711). The group of the metals is to be found in the Periodic Table to the left of the group of the semimetals, and thus includes the main-group metals, transition-group metals, lanthanides and actinides. The term mixed-metal oxide, nitride, etc. means here a chemical compound in which at least two metals and/or semimetals are joined to one another chemically together with the corresponding (non)metal anion (oxide, nitride, etc.).

The nanoscale fillers which can be used in accordance with the invention are preferably aluminum oxide, zirconium dioxide, titanium dioxide, zinc oxide, tin dioxide, cerium oxide, aluminum silicon oxides, silicon zinc oxides, silicon zirconium oxides, iron oxides and mixtures thereof with silicon dioxide, indium oxides and mixtures thereof with silicon dioxide and/or tin dioxide, silicon dioxide, boron nitride, strontium sulfate, barium sulfate, strontium titanate, barium titanate, sodium zirconate, potassium zirconate, magnesium zirconate, calcium zirconate, strontium zirconate, barium zirconate, sodium tungstate, potassium tungstate, magnesium tungstate, calcium tungstate, strontium tungstate and/or barium tungstate.

Nanoscale radiopaque fillers used with preference are selected from the group consisting of salts of the rare earth metals, of scandium, of yttrium, of barium and of strontium, or tungstates. Suitable low-solubility salts are preferably sulfates, phosphates or fluorides.

Among the salts of the rare earth metals (elements 57-71), of scandium or of yttrium, preference is given to the trifluorides. The preferred rare earth metals include lanthanum, cerium, samarium, gadolinium, dysprosium, erbium or ytterbium. Among their salts, preference is given to fluorides, especially ytterbium trifluoride (YbF3). Preferred barium salts and strontium salts are fluorides, phosphates and sulfates, more particularly the sulfates.

The expression "tungstate" encompasses metal compounds of the orthotungstates and polytungstates, the former being preferred.

The metal tungstate is preferably a tungstate compound of a polyvalent metal, more particularly of a divalent or trivalent metal. Suitable divalent metals include alkaline earth metals, such as magnesium, calcium, strontium or barium, more particularly calcium, strontium or barium. Strontium and barium tungstates are notable for particularly high radiopacity, since in these compounds two good contrast agents are combined with one another. Preferred trivalent metals comprise scandium, yttrium or rare earth metals, such as lanthanum, cerium, samarium, gadolinium, dysprosium, erbium or ytterbium. Here again, the radiopacity is particularly high on account of the fact that a good contrast agent (tungstate) is combined with a highly contrast-forming metal.

In addition it is possible to carry out metal atom doping of the tungstates (or else the other nanoscale salts) used in accordance with the invention. For this purpose, preferably, the host lattice metal is replaced by the dopant in an amount of up to 50 mol %, more preferably 0.1 to 40 mol %, even more preferably 0.5 to 30 mol %, more particularly 1 to 25 mol %. The dopant chosen may contribute to the radiopacity. For analytical reasons, however, it may also be of interest to choose one or more doping metals which impart luminescent properties, more particularly photoluminescence. Dopants suitable for this purpose are known in the art and are often selected from a lanthanide other than the host lattice metal. Examples include combined doping with Eu and Bi, or the doping of Ce in combination with Nd, Dy or Tb, or Er in combination with Yb. Equally it is possible to dope a tungstate as host lattice with a suitable lanthanide ion or another metal ion, e.g., $Bi^{3+}$ or $Ag^+$.

The nanoscale radiopaque fillers of the invention preferably have the following particle sizes or ranges of these particle sizes:
  less than 1000 nm, less than 700 nm, less than 500 nm, less than 200 nm, less than 100 nm, less than 25 nm,
  between 1 nm and 80 nm, between 4 nm and 60 nm, between 6 nm and 50 nm, between 0.5 nm and 22 nm, between 1 nm and 20 nm, between 1 nm and 10 nm or between 1 nm and 5 nm.

Suitable methods of particle size determination are numerous and known to the skilled person. Suitable methods are sedimentation in a gravity or centrifugal field (e.g., analytical ultracentrifugation), particle counting in an electrolyte (also called the Coulter counter method), image analysis [optical or electron-microscopical (e.g., TEM, REM, ESEM) or video image analysis], ultrasound spectroscopy or 3D-ORM laser backscattering. Preferred methods are light scattering methods, and among these static light scattering (e.g., laser diffraction or Mie scattering) or dynamic light scattering.

Particular preference is given to individual, unaggregated and unagglomerated nanoscale fillers. Preference extends to fillers with a unimodal particle size distribution.

The nanoscale filler of the invention has a BET surface area (to DIN 66131 or DIN ISO 9277) of between 15 $m^2/g$ and 600 $m^2/g$, preferably between 30 $m^2/g$ and 500 $m^2/g$, and more preferably between 50 $m^2/g$ and 400 $m^2/g$.

Suitable amounts of the nanoscale radiopaque filler in the infiltrant, based on the total mass of the infiltrant with all ingredients, are 1% to 30%, preferably 5% to 25%, more preferably 10% to 20% by weight; additionally preferred ranges are 1% to 5%, 5% to 10%, 10% to 15%, and 15% to 20% by weight.

The infiltrant of the invention may further comprise nanoscale fillers having a remineralizing effect. Preference is given to metal fluorides or (fluoro)(chloro)hydroxylapatites or else fluorine aluminum silicates.

The nanoscale filler may be organically modified.

In the case of this organic modification, functional groups are applied to the surface of the nanoparticles but on the one hand are attached either covalently or adsorbatively to the nanoparticles and which on the other hand may react chemically with the monomer matrix (organic binders) or else have a high affinity for the organic binder.

The organic modification of the surface of the nanofillers is accomplished preferably by treatment with a siloxane, chlorosilane, silazane, titanate, zirconate, tungstate or with an organic acid, such as, for example, organic phosphonic acid, or phosphoric acid, or organic acids as are described, for example, in U.S. Pat. No. 6,387,981, an organic acid chloride or acid anhydride. The siloxanes, chlorosilanes, silazanes, titanates, zirconates, and tungstates have with particular preference the following general formulae:

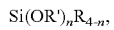

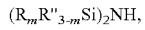

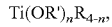

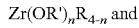 and

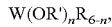

where
  m is 1, 2 or 3,
  n is 1, 2 or 3, n preferably being 3,
  the group R' attached via the oxygen, and the group R", is any desired organic functional group, preferably an alkyl group, more preferably a methyl, ethyl, propyl or isopropyl group, and
  the functional group R is any desired organic group and is attached directly via a carbon atom to the silicon, titanium, zirconium or tungsten.

If m or n is 1 or 2, the groups R may be alike or different. R is preferably selected such that it possesses one or more functional groups which are able to react chemically with monomers or which have a high affinity for the monomer matrix. These functional groups are also present in the above-recited organic acids, acid chlorides, and acid anhydrides that can likewise be used for the organic surface modification. The groups in question are preferably acrylate, methacrylate, cyanoacrylate, acrylamide, methacrylamide, vinyl, allyl, styryl, epoxy, oxetane, vinyl ether, amino, acid, acid ester, acid chloride, phosphate, phosphonate, phosphite, thiol, alcohol and/or isocyanate groups.

The infiltrant of the invention may further comprise radiopaque organic compounds known to the skilled worker. Suitable radiopaque organic compounds are organometallic compounds, aliphatic, cyclic or aromatic halides, more particularly bromine compounds, monomers comprising heavy metal ions, and also halogen-containing monomers. Preferred radiopaque organic compounds of the invention are (meth)acrylated triphenylbismuth derivatives and also iodine-substituted benzoic esters and benzamides.

Suitable monomers present in the infiltrant of the invention are selected from crosslinking monomers having two polymerizable groups and are preferably esters of acrylic and/or methacrylic acid. They may preferably be selected from the group consisting of DDDMA, 1,10-decanediol dimethacrylate; PEG400DA, polyethylene glycol 400 diacrylate; PEG400DMA, polyethylene glycol 400 dimethacrylate; PEG300DA, polyethylene glycol 300 diacrylate; PEG300DMA, polyethylene glycol 300 dimethacrylate; BPA (EO) 10DMA, ethoxylated (10) bisphenol A dimethacrylate; BPA(EO) 30DMA, ethoxylated (30) bisphenol A dimethacrylate; PEG200DA, polyethylene glycol 200 diacrylate; PEG600DA, polyethylene glycol 600 diacrylate, NPG(PO)$_2$DA, propoxylated (2) neopentylglycol diacrylate; BPA(EO)$_2$DA, ethoxylated (4) bisphenol A diacrylate; BPA (PO)$_2$DMA, propoxylated (2) bisphenol A dimethacrylate; bis-GMA, 2,2-bis[4-(2-hydroxy-3-methacryloyloxypropoxy)phenyl]propane; UDMA, 1,6-bis(methacryloyloxy-2-ethoxycarbonylamino)-2,4,4-trimethylhexane; EGDMA, ethylene glycol dimethacrylate; TEDMA, triethylene glycol dimethacrylate; 4EGDMA, tetraethylene glycol dimethacrylate; BDMA, 1,3-butylene glycol dimethacrylate; HDDMA, 1,6-hexanediol dimethacrylate; 1,4-butylenediol diacrylate; 4EDA, tetraethylene glycol diacrylate; NDDA, 1,9-nonanediol diacrylate; DEGDMA, diethylene glycol dimethacrylate; PDDMA, 1,5-pentanediol dimethacrylate; BDDMA, 1,4-butanediol dimethacrylate; PRDMA, 1,3-propanediol dimethacrylate; and dimethyloltricyclo[5.2.1.0]decane dimethacrylate.

Additionally suitable monomers present in the infiltrant of the invention are selected from crosslinking monomers having at least three polymerizable groups of the following formula

with the following definitions:
R$^1$ is a linear or branched hydrocarbon having 3-24 C atoms, comprising alkyl, cycloalkyl or aryl;
optionally containing O, N, Si, S, P as heteroatoms, examples being siloxane and/or cyclosiloxane and/or carbosilane and/or cyclocarbosilane and/or, in particular, ether groups or polyether groups, polyester groups, polysiloxane groups or polycarbosilane groups;
optionally substituted by hydroxyl and/or carbonyl and/or halogen (preferably fluorine) and/or ammonium-alkylene groups and/or siloxane and/or cyclosiloxane and/or carbosilane and/or cyclocarbosilane and/or acid groups or acid-derivative groups, more particularly carboxylic acid groups, phosphoric acid groups, phosphonic acid groups or sulfonic acid groups;
R$^2$ is a linear or branched hydrocarbon having 1-16 C atoms, comprising alkyl, cycloalkyl or aryl;
optionally containing O, N, Si, S, P as heteroatoms, examples being siloxane and/or cyclosiloxane and/or carbosilane and/or cyclocarbosilane and/or, in particular, ether groups or polyether groups, polyester groups, polysiloxane groups or polycarbosilane groups;
optionally substituted by hydroxyl and/or carbonyl and/or halogen (preferably fluorine) and/or ammonium-alkylene groups and/or siloxane and/or cyclosiloxane and/or carbosilane and/or cyclocarbosilane and/or acid groups or acid-derivative groups, more particularly carboxylic acid groups, phosphoric acid groups, phosphonic acid groups or sulfonic acid groups;
X is a linking group identically or differently selected from an ether group, carbonyl group, ester group, amide group, urethane group or urea group;
Y is a group identically or differently comprising a polymerizable double bond and/or a ring-openingly polymerizable group and/or a thiol group; preferably vinyl, (meth)acrylate, (meth)acrylamide or epoxide groups;
k is 0 or 1;
l is 0 or 1
m is at least 1;
n is at least 1
n×m is at least 3.

Suitable low-viscosity monomers having at least three polymerizable groups are, for example, TMPTMA, trimethylolpropane trimethacrylate; TMPTA, trimethylolpropane tri (meth)acrylate; DTMPTA, ditrimethylolpropane tetra(meth) acrylate; diPENTA, dipentaerythritol penta(meth)acrylate; or DPEHA, dipentaerythritol hexa(meth)acrylate.

Additionally suitable low-viscosity monomers having at least three polymerizable groups are based for example on alkoxylated multiple alcohols (tri-, tetra-, penta-, hexa-, polyols) such as trimethylolpropane, ditrimethylolpropane, glycerol, pentaerythritol or dipentaerythritol.

Particularly preferred are (meth)acrylic esters of alkoxylated multiple alcohols such as, for example, ethoxylated trimethylolpropane trimethacrylate, ethoxylated trimethylolpropane triacrylate, propoxylated trimethylolpropane trimethacrylate, propoxylated trimethylolpropane triacrylate, ethoxylated pentaerythritol trimethacrylate, ethoxylated pentaerythritol triacrylate, ethoxylated pentaerythritol tetramethacrylate, ethoxylated pentaerythritol tetraacrylate, ethoxylated dipentaerythritol trimethacrylate, ethoxylated dipentaerythritol tetramethacrylate, ethoxylated dipentaerythritol pentamethacrylate, ethoxylated dipentaerythritol hexamethacrylate, ethoxylated dipentaerythritol triacrylate, ethoxylated dipentaerythritol tetraacrylate, ethoxylated dipentaerythritol pentaacrylate, ethoxylated dipentaerythritol hexaacrylate, propoxylated pentaerythritol trimethacrylate, propoxylated pentaerythritol triacrylate, propoxylated pentaerythritol tetramethacrylate, propoxylated pentaerythritol tetraacrylate, propoxylated dipentaerythritol trimethacrylate, propoxylated dipentaerythritol tetramethacrylate, propoxylated dipentaerythritol pentamethacrylate, propoxylated dipentaerythritol hexamethacrylate, propoxylated dipentaerythritol triacrylate, propoxylated dipentaerythritol tetraacrylate, propoxylated dipentaerythritol pentaacrylate, and propoxylated dipentaerythritol hexaacrylate.

Alkoxy groups attached to alcohols represent (molecular-) chain extenders. Chain extension may be achieved preferably through ethoxylation or propoxylation. For chain extension there are further linking possibilities available, examples being ether bonds, ester bonds, amide bonds, urethane bonds, and the like, which may be followed preferably again by ethylene glycol groups or propylene glycol groups.

The chain-extending group is functionalized preferably terminally with the crosslinking groups, preferably with a methacrylate or an acrylate group, methacrylamide or acrylamide group.

A crosslinking point is regarded as being the position of the crosslinking polymerizable group—for example, the position of a C═C double bond in the monomer.

The chain length is preferably such that the distance between crosslinking points is at least 7, preferably at least 9, more preferably 10 to 30, with particular preference 11 to 21 bond lengths. The distance is preferably less than 50 bond lengths.

By distance between crosslinking points is meant the shortest distance between the crosslinking groups, as for example two C═C double bonds, along the molecule. The reference is therefore only to the constitution of the molecule, and not, say, to the actual spatial position of the groups relative to one another, as governed, for instance, by configuration or conformation.

By bond length is meant the distance between two atoms in the molecule, irrespective of the nature of the covalent bonding and of the exact length of the individual covalent bond.

The preferred fraction of these monomers is dependent on the number of crosslinking groups in the monomer mixture, on the size of the chain-extending groups, and on the resultant PC.

The infiltrant of the invention may further comprise monomers having one polymerizable group. These monomers may preferably be selected from the group consisting of MMA, methyl methacrylate; EMA, ethyl methacrylate; n-BMA, n-butyl methacrylate; IBMA, isobutyl methacrylate, t-BMA, tert-butyl methacrylate; EHMA, 2-ethylhexyl methacrylate, LMA, lauryl methacrylate; TDMA, tridecyl methacrylate; SMA, stearyl methacrylate; CHMA, cyclohexyl methacrylate; BZMA, benzyl methacrylate, IBXMA, isobornyl methacrylates; MAA, methacrylic acid; HEMA, 2-hydroxyethyl methacrylate; HPMA, 2-hydroxypropyl methacrylate; DMMA, dimethylaminoethyl methacrylate; DEMA, diethylaminoethyl methacrylate; GMA, glycidyl methacrylate; THFMA, tetrahydrofurfuryl methacrylate; AMA, allyl methacrylate; ETMA, ethoxyethyl methacrylate; 3FM, trifluoroethyl methacrylate; 8FM, octafluoropentyl methacrylate; AIB, isobutyl acrylate; TBA, tert-butyl acrylate; LA, lauryl acrylate; CEA, cetyl acrylate; STA, stearyl acrylate; CHA, cyclohexyl acrylate; BZA, benzyl acrylate; IBXA, isobornyl acrylate; 2-MTA, 2-methoxyethyl acrylate; ETA, 2-ethoxyethyl acrylate; EETA, ethoxyethoxyethyl acrylate; PEA, 2-phenoxyethyl acrylate; THFA, tetrahydrofurfuryl acrylate; HEA, 2-hydroxyethyl acrylate; HPA, 2-hydroxypropyl acrylate; 4HBA, 4-hydroxybutyl acrylate; DMA, dimethylaminoethyl acrylate; 3F, trifluoroethyl acrylate; 17F, heptadecafluorodecyl acrylate, 2-PEA, 2-phenoxyethyl acrylate; TBCH, 4-tert-butylcyclohexyl acrylate; DCPA, dihydrodicyclopentadienyl acrylate; EHA, 2-ethylhexyl acrylate; and 3EGMA, triethylene glycol monomethacrylate.

It may be of advantage if the monomers present in the infiltrant contain additional functional groups such as acid groups, more particularly carboxylic acid groups, phosphoric acid groups, phosphonic acid groups or sulfonic acid groups, or ammonium-alkylene groups or halogen, more particularly fluorinated alkylene.

The monomers, monomer mixtures and/or infiltrants preferably have a dynamic viscosity of less than 50 mPas, more preferably less than 30 mPas, with particular preference less than 15 mPas.

The fraction of crosslinking monomers having at least three polymerizable groups can be between 0% and 50% by weight, further between 10% and 30% by weight. The fraction of crosslinking monomers having two polymerizable groups is in one preferred embodiment between 100% and 50% by weight. Another preferred range is between 90% and 70% by weight.

The infiltrants of the invention may cure free-radically, anionically or cationically, depending on the chemical structure of the monomers they comprise. Preferably the monomers are curable free-radically or cationically.

The free-radical curing of the monomers of the invention can be accomplished by vinyl polymerization of suitable double bonds. Particularly suitable in this respect are (meth)acrylates, (meth)acrylamides, styryl compounds, cyanoacrylates, and compounds having similarly effectively free-radically polymerizable double bonds. A further possibility of free-radical curing lies in the ring-opening polymerization of cyclic vinyl compounds such as the vinylcyclopropanes described in EP 1 413 569, EP 1 741 419, and EP 1 688 125, or other cyclic systems such as vinylidene-substituted orthospiro carbonates or orthospiro esters. Another possibility also lies in the copolymerization of the ring-opening polymerizing systems with the aforementioned simply polymerizing double bonds. Free-radical curing may also be accomplished, furthermore, by a stage reaction known under the rubric of the thiolene reaction, as described in WO 2005/086911.

The cationic curing of the monomers of the invention may likewise be accomplished by both ring-opening polymerization and vinyl polymerization. Suitable vinyl polymers are vinyl ethers, styryl compounds, and other compounds having electron-rich vinyl groups. Suitable ring-openingly polymerizing monomers are compounds which carry epoxide, oxetane, aziridine, oxazoline or dioxolane groups. Further ring-openingly polymerizing groups may be taken from the literature, for example: K. J. Ivin, T. Saegusa, (eds.), Vol. 2, Elsevier Appl. Sci. Publ., London 1984. Particularly suitable are silicon-containing epoxide monomers, as described in WO 02/066535 or WO 2005/121200. Particularly advantageous in the context of the use of epoxides or oxetanes is the low polymerization contraction and also the low inhibition layer of these materials.

The mixing of different monomers likewise serves to fine-tune the mechanical properties such as hardness and strength, the depth of through-cure and/or the degree of polymerization, the residual monomer content, the extent of the lubricating layer, the contraction, the stability, the water absorption, and, in particular, the freedom from stress with retention of a high penetrativity (PC>50).

Also important in particular is the water compatibility of the monomers, in the case, for instance, where the enamel lesion still contains residual moisture after preparation (etching, rinsing, drying). Certain monomers can absorb residual moisture and so further improve penetration. Suitability for this purpose is possessed in particular by water-soluble and/or phase-mediating esters of (meth)acrylic acid, e.g., HEMA, 2-hydroxyethyl methacrylate, or GDMA, glycerol dimethacrylate, or GMA, glycerol monomethacrylate.

Mixing with further monomers may also serve in particular to fine-tune other advantageous properties such as high surface smoothness (plaque-preventing), fluoride release, radiopacity, adhesion to enamel, long-term color stability, biocompatibility, and so on.

The infiltrant may also comprise hyperbranched monomers, dendrimers for example, that are familiar in the dental sector and are known to the skilled worker from, for example, WO 02/062901, WO 2006/031972 or EP 1 714 633, especially in order to lower the residual monomer content and to enhance the biocompatibility.

The infiltrant may comprise bactericidal monomers that are customary in the dental sector and are known to the skilled worker from, for example, EP 1 285 947 or EP 1 849 450.

The monomer mixtures here have a PC>50, preferably >100, more preferably >200.

The infiltrant comprises agents for curing the infiltrant. The agents for curing may be initiators that are customary in the dental sector and are known to the skilled worker, more particularly photoactivated initiator systems, or else may be chemically activating initiators, or mixtures of the different systems. The initiators that can be used here may be, for example, photoinitiators. These are characterized in that they are able, through absorption of light in the wavelength range from 300 nm to 700 nm, preferably from 350 nm to 600 nm, and more preferably from 380 nm to 500 nm, and, optionally, through additional reaction with one or more coinitiators, to effect curing of the material. Preference is given here to using phosphine oxides, benzoin ethers, benzil ketals, acetophenones, benzophenones, thioxanthones, bisimidazoles, metallocenes, fluorones, a-dicarbonyl compounds, aryldiazonium salts, arylsulfonium salts, aryliodonium salts, ferrocenium salts, phenylphosphonium salts or a mixture of these compounds.

Particular preference is given to using diphenyl-2,4,6-trimethylbenzoylphosphine oxide, benzoin, benzoin alkyl ethers, benzil dialkyl ketals, a-hydroxyacetophenone, dialkoxyacetophenones, a-aminoacetophenones, isopropylthioxanthone, camphorquinone, phenylpropanedione, 5,7-diiodo-3-butoxy-6-fluorone, (eta-6-10-cumene)(eta-5-cyclopentadienyl)iron hexafluorophosphate, (eta-6-cumene)-(eta-5-cyclopentadienyl)iron tetrafluoroborate, (eta-6-cumene) (eta-5-cyclopentadienyl)iron hexafluoroantimonate, substituted diaryliodonium salts, triarylsulfonium salts or a mixture of these compounds.

Coinitiators used for photochemical curing are preferably tertiary amines, borates, organic phosphites, diaryliodonium compounds, thioxanthones, xanthenes, fluorenes, fluorones, α-dicarbonyl compounds, fused polyaromatics or a mixture of these compounds.

Particular preference is given to using N,N-dimethyl-p-toluolidine, N,N-dialkylalkylanilines, N,N-dihydroxyethyl-p-toluidine, 2-ethylhexyl p-(dimethylamino)benzoate, butyrylcholine triphenylbutylborate or a mixture of these compounds.

The infiltrant can be prepared from a kit having at least two components. Infiltrants comprising two components have the advantage that they can be formulated so as to be self-curing (chemical curing). In one embodiment a first component comprises monomers and chemically activable initiators and a second component comprises suitable activators.

For chemical curing at room temperature it is general practice to use a redox initiator system composed of one or more initiators and one or more coinitiators with activator function. For reasons of storage stability, initiator and/or initiators and coinitiator and/or coinitiators are incorporated into parts of the infiltrant of the invention that are spatially separate from one another, i.e., the material is a multicomponent material, preferably a two-component material. Initiator or initiators used are preferably inorganic and/or organic peroxides, inorganic and/or organic hydroperoxides, barbituric acid derivatives, malonylsulfamides, protic acids, Lewis or Broensted acids and/or compounds which release such acids, carbenium ion donors such as methyl triflate or triethyl perchlorate, for example, or a mixture of these compounds, and coinitiator or coinitiators used are preferably tertiary amines, heavy metal compounds, more particularly compounds of groups 8 and 9 of the Periodic Table ("iron group and copper group"), compounds having ionogenically bonded halogens or pseudohalogens, such as quaternary ammonium halides, for example, weak Broensted acids such as, for example, alcohols and water or a mixture of these compounds.

In one particularly simple embodiment the instrument for applying the infiltrant (application aid) to the tooth is coated or impregnated with the activator.

In a further embodiment a first component comprises monomers and, as initiators, salts of CH-acidic compounds such as barbituric acid derivatives, and a second component comprises monomers and an activating component, preferably a more strongly acidic acid than the CH-acidic compound.

In one particularly simple embodiment an instrument for applying the infiltrant (application aid) to the tooth comprises canulas containing a mixing chamber and/or mixing elements.

The infiltrant may comprise stabilizers. Preference is given to UV stabilizers. Suitable UV stabilizers are known to the skilled worker; cited here by way of example are Chimasorb® and Tinuvin® (Ciba).

The infiltrant may comprise solvents. Preference is given to volatile solvents such as, for example, alcohols, ketones, ethers, etc.

The infiltrant preferably contains less than approximately 20% by mass, more preferably less than approximately 10% by mass, with particular preference no solvent.

The infiltrant may comprise at least one fluorescent dye and/or color pigments, in order to improve the appearance and/or adapt it to the dental enamel. Suitable fluorescent colorants are known to the skilled person and described in US 2004/017928 A1, for example. The infiltrant may comprise other colorants, especially for the production of different tooth colors. The infiltrant may comprise color-changing dyes which indicate the infiltrated lesion and change color to indicate the curing of the infiltrant. Preferably the dye becomes colorless after the infiltrant is cured. The dye may be free-radically reactive.

The color change may also be dependent on other influences, such as on the pH, for example.

The dye may have adsorptive properties, particularly with respect to the dental enamel, and so accumulates in the upper layer of the lesion. In that case it is possible to see the color change more readily in the interdental region as well.

The dye may have nonadsorptive properties and may penetrate deeply into the lesion, thereby making it possible, for example, to monitor the penetration more effectively.

The infiltrant may comprise thermochromic and/or photochromic additives which indicate the infiltrated region on irradiation with corresponding light and/or on temperature change.

The invention further provides for the use of an infiltrant of the invention to treat and/or prevent carious enamel lesions. Such use may encompass the following steps:
1. removing a thin surface layer of the enamel lesion by etching agent
2. rinsing off the etching agent
3. drying the lesion with a drying agent
4. infiltrating the lesion with an infiltrant
5. removing excesses (optional)
6. curing the infiltrant
7. infiltrating the lesion with an infiltrant (optional)
8. removing excesses (optional)
9. curing the infiltrant (optional)
10. polishing the infiltrated lesion surface (optional).

In individual steps of the infiltration method the desired result may be improved further by application of sound and/or ultrasound, particularly with regard to fillers that are present.

Preferred etching agents are gels of strong acids such as hydrochloric acid.

Preferred drying agents are toxicologically unobjectionable solvents with a high vapor pressure. They are selected, for example, from alcohols, ketones, ethers, esters, etc. Particular preference is given to ethanol.

The drying agent may comprise constituents of the initiator system which remain in the lesion after the system has evaporated.

The drying agent may comprise a film-former.

After a first and/or second infiltration, it is possible, optionally, to apply a fillers-comprising sealant or lacquer which preferably has a penetration coefficient below 50, is compatible with the infiltrant, is cured separately or together with said infiltrant, and produces a good bond. The sealant or lacquer preferably comprises the radiopaque nanoscale fillers of the invention, preferably in higher amounts than the infiltrant. The sealant or lacquer may, however, also have other fillers, examples being barium- or strontium-containing inert dental glasses and/or ionomer glasses.

Infiltrants comprising fillers may likewise find use as fissure sealants.

The infiltrant may comprise antibacterial additives. These may have a bacteriostatic, bactericidal and/or antibiotic action. Examples are silver-bearing nanoparticles and/or mixed oxide particles, zinc oxide nanoparticles, mixed oxide particles, tin fluorides and zinc fluorides, or else benzalkonium, chlorhexidine or triclosan.

The invention additionally encompasses a kit for implementing the infiltration method. Said kit comprises
1. etching agent
2. drying agent
3. infiltrant The invention is illustrated below with reference to a number of examples.

Components Employed

| | |
|---|---|
| TEDMA | triethylene glycol dimethacrylate |
| E3HDDA | ethoxylated 1,6-hexanediol diacrylate |
| CQ | camphorquinone |
| EHA | ethylhexyl p-N,N-dimethylaminobenzoate |
| BHT | 2,6-di-tert-butylphenol |
| Ph3Bi | triphenylbismuth |
| YbF3 | ytterbium trifluoride (40 nm) |

Test Methods
Radio-Opacity

The determination of the radiopacity or radio-opacity took place in accordance with the provisions of EN ISO 4049:2000 (Polymer-based filling, restorative and luting materials). The infiltrants were exposed to a halogen lamp (Heraflash; Heraeus Kulzer) to produce specimens approximately 1 mm thick. The exact sample thickness was determined using a caliper rule. The specimens were placed together with an aluminum step wedge (purity>98% aluminum, with less than 0.1% copper fraction and less than 1% iron fraction) on an X-ray film (Ultraspeed DF-50 dental film, film sensitivity D, Kodak). Specimen, aluminum step wedge and film were irradiated from a distance of 400 mm with an analog single-phase X-ray instrument from Gendex for 0.4 s with X-rays with an acceleration voltage of 65 kV. Following the development and fixing of the film, the degrees of blackening of the images of the specimens and of the aluminum step wedge were measured, a blackening curve (degree of blackening against height of aluminum step) was plotted for the aluminum step wedge, and the values of the radio-opacities for each specimen were determined using the graph.

Curing

Using in each case about 0.3 g of initiator-containing infiltrant or Adper Scotchbond SE, cylindrical Teflon molds (5×10 mm high) were filled and were exposed from above with an LED lamp (Satelec Mini-LED, Acteon, max. 2000 mW/mm$^2$) for 60 s. A spatula was then used to monitor whether the test substances were cured.

Demineralized enamel can be regarded in simple terms as a porous solid. The penetration of a (Newtonian) liquid through a structure of this kind is influenced by the physical parameters of surface tension, contact angle, and viscosity (Buckton G., Interfacial phenomena in drug delivery and targeting. Chur, 1995), all of the measurements being performed at room temperature (23° C.).

Surface Tension

There are a very large number of methods of determining the surface tension. A distinction is made been static and dynamic measurement methods. The static methods include the ring method and the plate method. Dynamic methods frequently employed are the measurement of the height of rise in capillaries, the droplet volume tensiometer, and the method of the pendant drop and of the sessile drop (Gebhardt (1982), Grundlagen der physikalischen Chemie von Grenzflächen und Methoden zur Bestimmung grenzflächenenergetischer Größen, Frauenhofer IRB Verlag, Stuttgart). In the present application, the surface tension of the infiltrants was carried out by means of contour analysis on a pendant droplet (DSA 10, KRÜSS GmbH). The surface tension was measured on newly formed droplets over a time of 30 s, with one value being recorded about every 5 s. For this purpose the resins were delivered using a fine syringe and the droplet that formed was filmed with a digital camera. The surface tension was determined from the characteristic shape and size of the droplet in accordance with the Young-Laplace equation. For each resin, 3 measurements were carried out in this way, and their average was reported as the surface tension.

Density Determination

The densities of the infiltrants were determined using a pycnometer. For this purpose the density of air was deemed to be 0.0013 g/ml and the gravitational acceleration to be 9.8100 m/s$^2$.

Contact Angle

Each individual measurement was carried out using enamel from bovine teeth. For this purpose, bovine teeth were embedded in a synthetic resin and the enamel surface was wet-polished using a sanding machine (Struers GmbH) with abrasive papers (80, 500 and 1200 grades), thereby providing planar enamel surfaces approximately 0.5×1.0 cm in size for the contact angle measurements. Up until the time of measurement, the enamel samples were stored in distilled water, and prior to measurement they were dried with ethanol and compressed air.

The contact angle was measured using a video contact angle measuring instrument (DSA, KRÜSS GmbH). In this case a drop of the infiltrant was applied to the enamel surface using a microliter syringe, and within a period of 10 s up to 40 individual pictures of the droplet were taken, under computer control, and the contact angle was determined by means of droplet contour analysis software.

Dynamic Viscosity

The dynamic viscosity, also referred to as the absolute viscosity, is a measure of the viscousness of a liquid medium and is expressed by the viscosity constant $\eta$ with the unit Pas or Ns/m$^2$ (Wagner J: Physikalisches Anfängerpraktikum der Universität Heidelberg, 2004). The greater $\Theta$, the thicker, i.e. the less fluid, a liquid. The viscosity is dependent on the temperature. The infiltrants of the invention are liquids which do not comprise any components that generate a structural viscosity (shear thinning or dilatancy) and would therefore sharply lower the penetrativity. The infiltrants of the invention, then, are Newtonian liquids. Their dynamic viscosity is a physical constant which is dependent on the temperature but not also on the shear rate, as is characteristic of non-Newtonian liquids (see, for example, ISO 3219:1993, section 3 on page 1 under "Notes"). The fact that the viscosities are physical constants and the measurement method used (in accordance, for example, with ISO 3219:1993) to determine the dynamic viscosity is not a factor, is confirmed by, among other things, the value of the dynamic viscosity of the comparative example of the present application, containing 80% of TEDMA and 20% of the slightly higher-viscosity E3HDDA, whose value of 9.7 mPas (23° C.) is similar to that of the pure TEDMA, measurement by an alternative method, of 8.4 mPas (25° C.) in accordance with WO 2007/131725 A1.

In the case of the present application, the viscosity of the resins was measured at 23° C. using a dynamic plate/plate viscometer (Dynamic Stress Rheometer, Rheometric Scientific Inc.). Measurement took place in steady stress sweep mode with slot sizes of 0.1 to 0.5 mm in the range from 0 to 50 Pa shearing stress without preliminary shearing of the resins.

EXAMPLES 5 example infiltrants were prepared and the penetration coefficient (PC) and radio-opacity of them and of a reference material were determined. The reference used was Adper™ Scotchbond™ SE (3M ESPE AG, batch: 70-2010-5417-1), a dental adhesive comprising nanofillers. The composition of the infiltrants is specified in table 1. Penetration coefficient (PC) and radio-opacity are specified in table 2.

TABLE 1

| % by weight | Comparative example | Inventive examples | | | |
|---|---|---|---|---|---|
| | | 1 | 2 | 3 | 4 |
| TEDMA | 80 | 80 | 80 | 80 | 80 |
| E3HDDA | 20 | 20 | 20 | 20 | 20 |
| YbF3 | 0 | 10 | 20 | 0 | 10 |
| Ph3B | 0 | 0 | 0 | 25 | 12.5 |

The infiltrants were prepared by first stirring together the amounts of the monomers TEDMA and E3HDDA as indicated in table 1. The indicated amounts of Ph3Bi were added in portions and dissolved by means of a laboratory stirrer monomer mixture. YbF3 was dispersed with a Dispermat (VMA Getzmann, dispersing disc diameter 2 cm, 2000 revolutions) for 30 minutes, to give a homogeneous dispersion. For curing, 0.5% by weight CQ, 0.84% by weight EHA, and 0.002% by weight BHT were added to the infiltrants. The mixtures were then homogenized again.

TABLE 2

| | Reference* | Comparative example | Inventive examples | | | |
|---|---|---|---|---|---|---|
| | | | 1 | 2 | 3 | 4 |
| DSR viscosity [mPas] | 370 | 9.7 | 10.9 | 13.8 | 12.8 | 13.7 |
| Surface tension [mN/m] | 33 | 35.6 | 34.9 | 34.9 | 36.2 | 35.3 |
| Contact angle [°] | 5.1 | 2 | 2.5 | 2.6 | 2.4 | 2.3 |
| PC [cm/s] | 4 | 183 | 160 | 126 | 141 | 139 |
| Radio-opacity [%] | 117 | 10 | 113 | 148 | 122 | 118 |
| Curing - 60 s exposure | yes | yes | yes | yes | yes | yes |

*3M ESPE data in MSDS for Adper Scotchbond SE Liquid B: 15-25% surface-modified zirconium dioxide; 15-25% TEDMA, 10-15% di-HEMA-phosphate; 5-10% mixture of methacrylate-containing phosphoric esters, 5-15% trimethylolpropane trimethacrylate, 1-10% urethane dimethacrylate.

The reference material has a high radiopacity, but owing to the very low PC is unsuitable or very poorly suitable for the infiltration of enamel lesions (for example in order to penetrate with sufficient depth into an enamel lesion).

Owing to the high PC, the infiltrant of the comparative example is particularly suited to the infiltration of enamel lesions. However, it has a very low radiopacity; a lesion infiltrated with this infiltrant is indistinguishable in the X-ray image from an untreated lesion.

The infiltrants of examples 1-4, of the invention, are highly suitable for the infiltration of enamel lesions, on the basis of the high PC, and in addition they also have a high radiopacity, which makes it readily possible, on the basis of an X-ray image, to distinguish between infiltrated regions and carious lesion.

The invention claimed is:

1. An infiltrant for dental application that comprises crosslinking monomers and initiator and, under measurement of the dynamic viscosity at room temperature, has a penetration coefficient PC>50 cm/s, wherein the infiltrant comprises at least one nanoscale radiopaque filler and/or radiopaque organic compound.

2. The infiltrant of claim 1, wherein said infiltrant has an ISO 4049 radio-opacity of at least 50% of aluminum.

3. The infiltrant of claim 1, wherein said at least one nanoscale radiopaque filler comprises metal, semimetal or mixed-metal oxides, silicates, nitrides, sulfates, titanates, zirconates, stannates, tungstates, phosphates, halides or a mixture thereof.

4. The infiltrant of claim 1, wherein the fillers are selected from the group consisting of aluminum oxide, zirconium dioxide, titanium dioxide, zinc oxide, tin dioxide, cerium oxide, aluminum silicon oxides, silicon zinc oxides, silicon zirconium oxides, iron oxides and mixtures thereof with silicon dioxide, indium oxides and mixtures thereof with silicon dioxide and/or tin dioxide, silicon dioxide, boron nitride, strontium sulfate, barium sulfate, strontium titanate, barium titanate, sodium zirconate, potassium zirconate, magnesium zirconate, calcium zirconate, strontium zirconate, barium zirconate, sodium tungstate, potassium tungstate, magnesium tungstate, calcium tungstate, strontium tungstate and/or barium tungstate.

5. The infiltrant of claim 1, wherein the nanoscale radiopaque fillers are salts.

6. The infiltrant of claim 5, wherein the salts are selected from the group consisting of sulfates, phosphates or fluorides of the rare earth metals.

7. The infiltrant of claim 6, wherein the rare earth metals are selected from the group consisting of the group consisting of lanthanum, cerium, samarium, gadolinium, dysprosium, erbium or ytterbium.

8. The infiltrant of claim 6, wherein the rare earth metals are selected from the group consisting of scandium, of yttrium, of barium, and strontium, tungstates, and orthotungstates.

9. The infiltrant of claim 6, wherein the nanoscale radiopaque filler salts are tungstates, and wherein said tungstates are doped with metal atoms of at least one metal, and wherein the host lattice metal of the filler salt is replaced by the dopant in an amount of up to 50 mol %.

10. The infiltrant of claim 9, wherein the host lattice metal of the filler salt is replaced by the dopant in an amount of 0.1 to 40 mol %.

11. The infiltrant of claim 9, wherein the host lattice metal of the filler salt is replaced by the dopant in an amount of 0.5 to 30 mol %.

12. The infiltrant of claim 9, wherein the host lattice metal of the filler salt is replaced by the dopant in an amount of 1 to 25 mol %.

13. The infiltrant of claim 1, wherein the radiopaque nanoscale filler has a particle size of less than 1000 nm.

14. The infiltrant of claim 1, wherein the radiopaque nanoscale filler has a particle size of less than 700 nm.

15. The infiltrant of claim 1, wherein the radiopaque nanoscale filler has a particle size of less than 500 nm.

16. The infiltrant of claim 1, wherein the radiopaque nanoscale filler has a particle size of less than 200 nm.

17. The infiltrant of claim 1, wherein the radiopaque nanoscale filler has a particle size of less than 100 nm.

18. The infiltrant of claim 1, wherein the radiopaque nanoscale filler has a particle size of between 0.5 nm and 80 nm.

19. The infiltrant of claim 1, wherein the radiopaque nanoscale filler has a particle size of between 0.5 nm and 60 nm.

20. The infiltrant of claim 1, wherein the radiopaque nanoscale filler has a particle size of between 0.5 nm and 50 nm.

21. The infiltrant of claim 1, wherein the radiopaque nanoscale filler has a particle size of between 0.5 nm and 22 nm.

22. The infiltrant of claim 1, wherein the radiopaque nanoscale filler has a particle size of between 1 nm and 20 nm.

23. The infiltrant of claim 1, wherein the radiopaque nanoscale filler has a particle size of between 1 nm and 10 nm.

24. The infiltrant of claim 1, wherein the radiopaque nanoscale filler has a particle size of between 1 nm and 5 nm.

25. The infiltrant of claim 1, wherein the radiopaque nanoscale filler comprises individual, unaggregated and unagglomerated nanoscale filler particles.

26. The infiltrant of claim 25, wherein the radiopaque nanoscale filler has a unimodal particle size distribution.

27. The infiltrant of claim 1, wherein the radiopaque nanoscale filler has a DIN 66131 or DIN ISO 9277 BET surface area of between 15 m$^2$/g and 600 m$^2$/g.

28. The infiltrant of claim 1, wherein the radiopaque nanoscale filler has a DIN 66131 or DIN ISO 9277 BET surface area of between 30 m$^2$/g and 500 m$^2$/g.

29. The infiltrant of claim 1, wherein the radiopaque nanoscale filler has a DIN 66131 or DIN ISO 9277 BET surface area of between 50 m$^2$/g and 400 m$^2$/g.

30. The infiltrant of claim 1, wherein the amount of the nanoscale radiopaque filler in the infiltrant, based on the total mass of the infiltrant with all ingredients, is 1% to 30% by weight.

31. The infiltrant of claim 1, wherein the amount of the nanoscale radiopaque filler in the infiltrant, based on the total mass of the infiltrant with all ingredients, is 5% to 25% by weight.

32. The infiltrant of claim 1, wherein the amount of the nanoscale radiopaque filler in the infiltrant, based on the total mass of the infiltrant with all ingredients, is 10% to 20% by weight.

33. The infiltrant of claim 1, wherein the amount of the nanoscale radiopaque filler in the infiltrant, based on the total mass of the infiltrant with all ingredients, is 1% to 5% by weight.

34. The infiltrant of claim 1, wherein the amount of the nanoscale radiopaque filler in the infiltrant, based on the total mass of the infiltrant with all ingredients, is 5% to 10% by weight.

35. The infiltrant of claim 1, wherein the amount of the nanoscale radiopaque filler in the infiltrant, based on the total mass of the infiltrant with all ingredients, is 10% to 15% by weight.

36. The infiltrant of claim 1, wherein the amount of the nanoscale radiopaque filler in the infiltrant, based on the total mass of the infiltrant with all ingredients, is 15% to 20% by weight.

37. The infiltrant of claim 1, wherein the radiopaque nanoscale filler is organically modified.

38. The infiltrant of claim 37, wherein the radiopaque nanoscale filler is organically modified by treatment with a siloxane, chlorosilane, silazane, titanate, zirconate, tungstate or with an organic acid, an organic acid chloride or acid anhydride.

39. The infiltrant of claim 38, wherein the siloxanes, chlorosilanes, silazanes, titanates, zirconates, and tungstates having the following general formulae:

$$Si(OR')_n R_{4-n},$$

$$SiCl_n R_{4-n},$$

$$(R_m R_{3-m}'Si)_2 NH,$$

$$Ti(OR')_n R_{4-n},$$

$$Zr(OR')_n R_{4-n} \text{ and}$$

$$W(OR')_n R_{6-n},$$

where
m is 1, 2 or 3,
n is 1, 2 or 3,
the group R' attached via the oxygen, and the group R', is an organic functional group, and
the functional group R is an organic group and is attached directly via a carbon atom to the silicon, titanium, zirconium or tungsten.

40. The infiltrant of claim 39, wherein R' is an alkyl group.

41. The infiltrant of claim 40, wherein said alkyl group is selected from the group consisting of methyl, ethyl, propyl and isopropyl groups.

42. The infiltrant of claim 1, wherein the radiopaque organic compound is selected from the group consisting of
organometallic compounds,
aliphatic, cyclic or aromatic halides, more particularly bromine compounds,
monomers comprising heavy metal ions and/or halogens.

43. The infiltrant of claim 42, wherein said monomers comprising halogens comprise one or more of (meth)acrylated triphenylbismuth derivatives, iodine-substituted benzoic esters and benzamides.

44. The infiltrant of claim 1, wherein said infiltrant has a penetration coefficient PC>100 cm/s.

45. The infiltrant of claim 1, wherein said infiltrant has a dynamic viscosity as measured at room temperature of 50 mPas or less.

46. The infiltrant of claim 1, wherein said infiltrant has a dynamic viscosity as measured at room temperature of 30 mPas or less.

47. The infiltrant of claim 1, wherein said infiltrant has a dynamic viscosity as measured at room temperature of 15 mPas or less.

48. Kit for preparing an infiltrant according to any of the preceding claims, wherein the kit comprises
a first component with monomers and chemically activable initiators and
a second component with activators.

49. The kit of claim 48, further comprising an etching and/or drying agent.

50. A method of treating and/or preventing carious enamel lesions and/or sealing dental fissures comprising treating a tooth surface with the infiltrant of claim 1.

* * * * *